(12) United States Patent
Sugiura

(10) Patent No.: US 8,110,205 B2
(45) Date of Patent: Feb. 7, 2012

(54) SILVER-CONTAINING INORGANIC ANTIBACTERIAL

(75) Inventor: Koji Sugiura, Nagoya (JP)

(73) Assignee: Toagosei Co., Ltd., Tokyo (JP)

( * ) Notice: Subject to any disclaimer, the term of this patent is extended or adjusted under 35 U.S.C. 154(b) by 114 days.

(21) Appl. No.: 12/681,668

(22) PCT Filed: Oct. 5, 2007

(86) PCT No.: PCT/JP2007/069552
§ 371 (c)(1),
(2), (4) Date: Apr. 5, 2010

(87) PCT Pub. No.: WO2009/044477
PCT Pub. Date: Apr. 9, 2009

(65) Prior Publication Data
US 2010/0272828 A1    Oct. 28, 2010

(51) Int. Cl.
*A61K 31/42* (2006.01)
*A61P 31/04* (2006.01)

(52) U.S. Cl. ..................... 424/400; 424/604

(58) Field of Classification Search ............. 424/400
See application file for complete search history.

(56) References Cited

U.S. PATENT DOCUMENTS

| | | | |
|---|---|---|---|
| 5,296,238 A | 3/1994 | Sugiura et al. | |
| 5,441,717 A | 8/1995 | Ohsumi et al. | |
| 7,771,738 B2 * | 8/2010 | Sugiura et al. | 424/405 |
| 2006/0182812 A1 | 8/2006 | Ono | |

FOREIGN PATENT DOCUMENTS

| | | |
|---|---|---|
| JP | 60-239313 A | 11/1985 |
| JP | 03-83906 A | 4/1991 |
| JP | 05-17112 A | 1/1993 |
| JP | 06-40829 A | 2/1994 |
| JP | 06-48713 A | 2/1994 |
| TW | 200418718 | 10/2004 |
| WO | 2006/118159 A1 | 11/2006 |

OTHER PUBLICATIONS

Office Action in corresponding Taiwan Application (Chinese), Jun. 24, 2011.
Jager, C. et al.,"31P and 29Si NMR Investigations of the Structure of NASICON-Compounds", Expermentelle Technik der Physik, 1988, vol. 36, No. 4/5, p. 339-348.
Jager, C. et al., "31P MAS NMR Study of the NASICON System Na1+4yZr2-y(PO4)3", Chemical Physics Letters, 1988, vol. 150, No. 6, p. 503-505.
H. Y-P. Hong, "Crystal Structures and Crystal Chemistry in the Sistem Na1+xZr2SixP3-xO12", Mat. Res. Bull, 1976, vol. 11, p. 173-182.
International Search Report issued on Dec. 4, 2007 in International Application No. PCT/JP2007/069552.

* cited by examiner

*Primary Examiner* — Scott Long
*Assistant Examiner* — Sarah Alawadi
(74) *Attorney, Agent, or Firm* — Fitch, Even, Tabin & Flannery

(57) ABSTRACT

The present invention is completed by finding that a silver ion-containing zirconium phosphate represented by the following formula (1) is excellent in heat resistance and chemical resistance, low in resin coloring and excellent in processability.

$$Ag_a M_b Zr_c Hf_d (PO_4)_3 \cdot n H_2 O \qquad (1)$$

wherein, in the formula (1), M is at least one ion selected from alkali metal ion, hydrogen ion and ammonium ion, a, b, c and d are positive numbers satisfying $a+b+4(c+d)=9$; c and d satisfy $1.75<(c+d)<2.25$; and n is 0 or a positive number of not more than 2.

4 Claims, No Drawings

SILVER-CONTAINING INORGANIC ANTIBACTERIAL

CROSS-REFERENCE TO RELATED APPLICATION

This application is a U.S. National Phase entry of International Application No. PCT/JP2007/069552 filed on Oct. 5, 2007, the complete disclosure of which is incorporated herein by reference.

TECHNICAL FIELD

The present invention relates to a compound retaining a silver ion on a zirconium phosphate by ion exchange, and provides a novel silver based inorganic antibacterial agent excellent in heat resistance, chemical resistance and processability, and also low in coloring when blended with a plastic.

BACKGROUND ART

Recently, zirconium phosphate based inorganic ion exchangers have been utilized in various applications by virtue of their features. Zirconium phosphate based inorganic ion exchangers include amorphous ones, crystalline ones having a two-dimensional layer structure and crystalline ones having a three-dimensional network structure. Above all, hexagonal zirconium phosphates which have a three-dimensional network structure are excellent in heat resistance, chemical resistance and radiation resistance and low in thermal expansion, and are applied to immobilization of radioactive waste, solid electrolytes, gas adsorption/separation agents, catalysts, a raw material for antibacterial agents, and so on.

Hitherto, various hexagonal zirconium phosphates have been known. For example, there are $A_xNH_{4(1-x)}Zr_2(PO_4)_3 \cdot nH_2O$ (for example, refer to Patent Document 1), $AZr_2(PO_4)_3 \cdot nH_2O$ (for example, refer to Patent Document 2) and $H_nR_{1-n}Zr_2(PO_4)_3 \cdot mH_2O$ (for example, refer to Patent Document 3).

Also, zirconium phosphates which differ in a ratio of Zr to P have been known. For example, there are $Na_{1+4x}Zr_{2-x}(PO_4)_3$ (for example, refer to Non-Patent Document 1), $Na_{1+2x}Mg_xZr_{2-x}(PO_4)_3$ (for example, refer to Non-Patent Documents 1 and 2) and $Na_{1+x}Zr_2Si_xP_{3-x}O_{12}$ (for example, refer to Non-Patent Documents 2 and 3).

As methods for synthesizing these hexagonal zirconium phosphates, have been known a calcining method in which raw materials are mixed, and thereafter calcined at not less than 1000° C. using a calcining furnace to effect the synthesis, a hydrothermal method in which raw materials are mixed in water or in a state of containing water, and thereafter pressurized and heated to effect the synthesis, and a wet method in which raw materials are mixed in water, and thereafter heated at atmospheric pressure to effect the synthesis.

Above all, the calcining method makes it possible to synthesize zirconium phosphates with an appropriately controlled P/Zr ratio just by mixing raw materials and heating them at a high temperature. However, in the calcining method, uniform mixing of raw materials is not easy, and zirconium phosphate with a homogeneous composition is hardly made. Further, the calcining method requires pulverization and classification in order to obtain products in grain form after calcining, and thus it had problems in quality and productivity. Also, as a matter of course, crystalline zirconium phosphates containing ammonia cannot be synthesized in the calcining method. On the other hand, in the wet or hydrothermal method, a homogeneous microparticulate zirconium phosphate can be obtained, but no crystalline zirconium phosphates have been obtained except those having a P/Zr ratio of 1.5 and those indicated by the following formula (3) with a P/Zr ratio of 2.

$$NH_4ZrH(PO_4)_2 \quad (3)$$

Ions such as of silver, copper, zinc, tin, mercury, lead, iron, cobalt, nickel, manganese, arsenic, antimony, bismuth, barium, cadmium and chromium have been known for a long time as metal ions that indicate antifungal, antibacterial and anti-algae properties (hereinafter, abbreviated to antibacterial metal ions). Especially, silver ion has been widely utilized as an aqueous silver nitrate solution which has effects of disinfection and sterilization. However, metal ions that show the above antifungal, antibacterial or anti-algae property are mostly toxic to human body, and thus there have been various limitations on methods of use, methods of storage, methods of disposing and the like, and applications also have been limited.

In order to exhibit the antifungal, antibacterial or anti-algae property, only a very small amount of antibacterial metal has to be allowed to act on an object of interest. Because of this, as antibacterial agents having the antifungal, antibacterial or anti-algae property, there have been proposed organic carrier based antibacterial agents in which an antibacterial metal ion is carried on an ion exchange resin, a chelate resin or the like, as well as inorganic antibacterial agents in which an antibacterial metal ion is carried on a clay mineral, an inorganic ion exchanger or a porous body.

Of the above various antibacterial agents, inorganic antibacterial agents are characteristic in that they are high in safety, long in durability of antibacterial effect, and also excellent in heat resistance, compared to organic carrier based antibacterial agents.

As one of the inorganic antibacterial agents, has been known an antibacterial agent comprising a clay mineral such as montmorillonite and zeolite in which alkali metal ions such as sodium ion have been ion-exchanged with silver ion. Since it has a skeleton structure based on the clay mineral itself which is inferior in acid resistance, it easily elutes silver ion and thus lacks durability of antibacterial effect, for example, in an acidic solution.

In addition, since the silver ion is unstable upon exposure to heat and light and immediately reduced to a metal silver, thereby causing coloring or the like, it had a problem in long term stability.

There has been one in which silver ion and ammonium ion are co-existent and carried on zeolite by ion exchange in order to enhance the stability of the silver ion. However, even in this case, prevention of coloring does not come to a practical level, and thus no solution has been given fundamentally.

Further, there have been other antibacterial agents in which an antibacterial metal is carried on an adsorptive charcoal. However, since these agents carry soluble antibacterial metal salts which physically adsorb or stick thereto, they rapidly elute antibacterial metal ions and thus lack durability of antibacterial effect when they are brought into contact with moisture.

Recently, an antibacterial agent in which an antibacterial metal ion is carried on a special zirconium phosphate salt has been proposed. For example, one represented by the following formula (4) has been known (for example, refer to Patent Document 4):

$$M^1M^2_xH_yA_z(PO_4)_2 \cdot nH_2O \quad (4)$$

wherein, in the formula (4), $M^1$ is one selected from tetravalent metals, $M^2$ is one selected from a silver, copper, zinc, tin, mercury, lead, iron, cobalt, nickel, manganese, arsenic, antimony, bismuth, barium, cadmium or chromium, A is one selected from alkali metal ions or alkaline earth metal ions, n is a number satisfying $0 \leq n \leq 6$, and x, y and z are numbers satisfying $0<(1)X(x)<2$, $0<y<2$, $0<z<0.5$ and $(1)X(x)+y+z=2$, provided that 1 is the valence number of $M^2$.

This antibacterial agent is known as a material which is chemically and physically stable, and shows antifungal and antibacterial properties for a long time. However, when this antibacterial agent is kneaded into a synthetic resin such as nylon, the resin is often colored as a whole so that it cannot be used as a product.

Patent Document 1: JP-A-H06-48713
Patent document 2: JP-A-H05-17112
Patent Document 3: JP-A-S60-239313
Patent Document 4: JP-A-H03-83906
Non-Patent Document 1: C. JAGER, and three others, "31P and 29Si NMR Investigations of the Structure of NASICON-Strukturtyps", Expermentelle Technik der Physik, 1988, Vol. 36, 4/5, p 339-348
Non-Patent Document 2: C. JAGER, and two others, "31P MAS NMR STUDY OF THE NASICON SYSTEM Na1+4yZr2-y(PO4)3", Chemical Physics Letters, 1988, Vol. 150, 6, p 503-505
Non-Patent Document 3: H. Y-P. HONG, "CRYSTAL STRUCTURE AND CRYSTAL CHEMISTRY IN THE SISTEM Na1+xZr2SixP3-xO12", Mat. Res. Bull, Vol. 11, p-173-182

DISCLOSURE OF THE INVENTION

Problems to be Solved by the Invention

The present invention aims at providing a silver based inorganic antibacterial agent excellent in heat resistance and chemical resistance, lowered in resin coloring and excellent in processability.

Means for Solving the Problem

As a result of intensive studies to solve the problem described above, the present inventor has found that the problem can be solved by a zirconium phosphate which contains silver ion with hafnium, as represented by the general formula (1) shown below:

$$Ag_a M_b Zr_c Hf_d (PO_4)_3 \cdot nH_2O \quad (1)$$

wherein, in the formula (1), M is at least one ion selected from alkali metal ion, hydrogen ion and ammonium ion, a, b, c and d are positive numbers satisfying $a+b+4(c+d)=9$; c and d satisfy $1.75<(c+d)<2.25$; and n is 0 or a positive number of not more than 2.

Therefore, the present invention provides a silver based inorganic antibacterial agent which comprises, as an effective ingredient, a compound represented by the above general formula (1).

In addition, according to a preferable embodiment of the present invention, a silver based inorganic antibacterial agent which comprises a silver ion retained by ion exchange on a zirconium phosphate represented by the general formula (2) shown below:

$$M_{b1} Zr_c Hf_d (PO_4)_3 \cdot nH_2O \quad (2)$$

wherein, in the formula (2), M is at least one ion selected from alkali metal ion, hydrogen ion and ammonium ion, b1, c and d are positive numbers satisfying $b1+4(c+d)=9$; c and d satisfy $1.75<(c+d)<2.25$; and n is a positive number of not more than 2.

In addition, according to another preferable embodiment of the present invention, the zirconium phosphate represented by the above general formula (2) is a zirconium phosphate produced by a wet synthesis method or hydrothermal synthesis method, and a silver based inorganic antibacterial agent is provided by retaining a silver ion on the zirconium phosphate by ion exchange.

In another aspect, the present invention provides an antibacterial product which contains the silver based inorganic antibacterial agent as defined above.

Effect of the Invention

The present silver based inorganic antibacterial agent which contains hafnium is excellent in antibacterial activity and prevention of coloring compared with conventional zirconium phosphate based antibacterial agents.

BEST MODE FOR CARRYING OUT THE INVENTION

Hereinafter, the present invention will be described. The silver based inorganic antibacterial agent of the present invention is represented by the general formula (1) shown above.

In the formula (1), M is at least one selected from the group consisting of alkali metal ion, hydrogen ion and ammonium ion, and more preferably comprises alkali metal ion and hydrogen ion from the viewpoint of ion exchangeability with silver ion and ease of synthesis.

In the formula (1), the alkali metal ion represented by M is exemplified by Li, Na, K, Rb and Cs, and these can be used alone or in combination of two or more. Of these, a preferable alkali metal ion is Na ion or K ion and more preferably Na ion from the viewpoint of ion exchangeability with silver ion and ease of synthesis.

In the formula (1), a is a positive number, preferably not less than 0.01 and more preferably not less than 0.03, and a is preferably not more than 1 and more preferably not more than 0.6. In the formula (1), when a is less than 0.01, antibacterial property may not be exhibited sufficiently.

In the formula (1), b is a positive number, preferably not less than 0.1 and more preferably not less than 0.3. When b is less than 0.1, discoloration may occur easily. In addition, b is preferably less than 2, more preferably not more than 1.8, further preferably not more than 1.72 and particularly preferably not more than 1.5.

In the formula (1), b is the total number of alkali metal ion, hydrogen ion and/or ammonium ion. When ammonium ion exists, there may be the case where no hydrogen ion exists, but it is preferable that the number of hydrogen ion is greater compared with alkali metal ion.

When no ammonium ion exists, there may be the case where no hydrogen ion exists, but it is preferably that the number of hydrogen ion is greater than compared with alkali metal ion. Meanwhile, when no ammonium ion exists, it is preferable that hydrogen ion exists.

In the present invention, alkali metal ion is preferably less than 2, more preferably less than 1.8, further more preferably less than 1.4, and preferably not less than 0.01, more preferably not less than 0.03 and further more preferably not less than 0.05, in terms of b of the formula (1).

In the present invention, hydrogen ion is preferably less than 2, more preferably less than 1.8, further more preferably less than 1.4, and preferably not less than 0.01, more preferably not less than 0.03 and further more preferably not less than 0.05, in terms of b of the formula (1).

In the present invention, ammonium ion is preferably less than 1, more preferably less than 0.8, further more preferably less than 0.4, and preferably not less than 0.01, more preferably not less than 0.03 and further more preferably not less than 0.05, in terms of b of the formula (1).

In the formula (1), c and d satisfy $1.75<(c+d)<2.25$, preferably more than 1.8, more preferably not less than 1.82 and further more preferably not less than 1.85. Also, c is preferably less than 2.2, more preferably not more than 2.1 and further more preferably not more than 2.05.

When c+d is not more than 1.75, a homogeneous zirconium phosphate represented by the formula (2) may hardly be obtained. Also, in the formula (1), d is preferably not more than 0.2, more preferably 0.001-0.15 and further more preferably 0.005-0.1. This range is preferable because the present antibacterial agent can be obtained.

In the formula (1), n is preferably not more than 1, more preferably 0.01-0.5 and further more preferably 0.03-0.3. When n exceeds 2, the silver based inorganic antibacterial agent of the present invention contains a large absolute amount of moisture, and thus may cause foaming, hydrolysis or the like during processing and the like.

As the zirconium phosphate used for synthesizing the silver based inorganic antibacterial agent of the present invention, one represented by the above formula (2) is preferably used.

In the formula (2), M is at least one selected from alkali metal ion, hydrogen ion and ammonium ion, b1, c and d are positive numbers satisfying $b1+4(c+d)=9$, c and d satisfy $1.75<(c+d)<2.25$, and n is a positive number of not more than 2. b1 satisfies $b1=a+b$ (a and b are the same as in the formula (1)). Also, in the formula (2), c and d are the same as in the formula (1).

The method for synthesizing the zirconium phosphate represented by the formula (2) includes wet methods or hydrothermal methods in which various raw materials are reacted in an aqueous solution. Concretely, a wet method is practiced by adjusting a pH of an aqueous solution containing predetermined amounts of a zirconium compound, a hafnium compound, an alkali metal compound, ammonia or a salt thereof, oxalic acid or a salt thereof, and phosphoric acid or a salt thereof to not more than 4, and then heating it at a temperature of not less than 70° C. under atmospheric pressure. On the other hand, a hydrothermal method can be practiced by adjusting a pH of an aqueous solution containing predetermined amounts of a zirconium compound, a hafnium compound, an alkali metal compound, ammonia or a salt thereof, oxalic acid or a salt thereof, and phosphoric acid or a salt thereof to not more than 4, and then heating it at a temperature of not less than 100° C. under pressure. Meanwhile, in case of hydrothermal method, the zirconium phosphate can be synthesized without adding oxalic acid or a salt thereof. The zirconium phosphate that has been synthesized is further filtered, well washed with water, dried and lightly pulverized to obtain a white microparticulate zirconium phosphate.

Zirconium compounds usable as a raw material for synthesis of the zirconium phosphate represented by the formula (2) are exemplified by zirconium nitrate, zirconium acetate, zirconium sulfate, basic zirconium sulfate, zirconium oxysulfate and zirconium oxychloride, and in consideration of reactivity and economy, preferably zirconium oxychloride.

Raw materials for hafnium usable as a raw material for synthesis of the zirconium phosphate represented by the formula (2) are water-soluble or acid-soluble hafnium salts and exemplified by hafnium chloride, hafnium oxychloride, hafnium ethoxide and the like, and a zirconium compound containing hafnium can also be used. Particularly, the zirconium compound containing hafnium is preferable, and in consideration of reactivity and economy, more preferable is zirconium oxychloride containing hafnium. In the present invention, a content of hafnium is preferably not less than 0.2% and not more than 5%, and more preferably not less than 1% and not more than 4% relative to zirconium, from the viewpoint of the performance of the resulting silver based inorganic antibacterial agent.

The content of hafnium in the formula (1) is preferably comparable to the content in the formula (2) that is used in synthesis.

Oxalic acid or a salt thereof usable as a raw material for synthesis of the zirconium phosphate represented by the formula (2) are exemplified by oxalic acid dihydrate, sodium oxalate, ammonium oxalate, sodium hydrogen oxalate and ammonium hydrogen oxalate, and preferably oxalic acid dihydrate.

Alkali metal compounds usable as a raw material for synthesis of the zirconium phosphate represented by the formula (2) are preferably sodium chloride, sodium nitrate, sodium sulfate, sodium hydroxide, potassium chloride, potassium nitrate, potassium sulfate or potassium hydroxide, and more preferably sodium hydroxide.

Ammonia or a salt thereof usable as a raw material for synthesis of the zirconium phosphate represented by the formula (2) are exemplified by ammonium chloride, ammonium nitrate, ammonium sulfate, aqueous ammonia, ammonium oxalate, ammonium dihydrogen phosphate, ammonium phosphate dibasic and ammonium phosphate, and preferably ammonium chloride or aqueous ammonia.

Phosphoric acid or a salt thereof usable as a raw material for synthesis of the zirconium phosphate represented by the formula (2) are preferably a soluble or acid-soluble salt which is exemplified by phosphoric acid, sodium phosphate, potassium phosphate and ammonium phosphate, and more preferably phosphoric acid. Meanwhile, the concentration of the phosphoric acid is preferably a concentration of about 60-85%.

Upon synthesis of the zirconium phosphate represented by the formula (2), a molar ratio of the phosphoric acid or a salt thereof to the zirconium compound (assuming that the zirconium compound is 1) is usually more than 1.3 and less than 2, more preferably 1.4 to less than 1.71, further more preferably 1.45-1.67, and particularly preferably 1.48-1.65.

That is, a preferable synthesis method of the zirconium phosphate represented by the formula (2) is a wet method or hydrothermal method in which the molar amount of phosphoric acid or salt thereof per 1 mole of zirconium compound is in a range between more than 1.3 and less than 2.

Upon synthesis of the zirconium phosphate represented by the formula (2), a molar ratio of phosphoric acid or salt thereof to ammonia or salt thereof (assuming that ammonia or salt thereof is 1) is preferably 0.3-10, further more preferably 1-10 and particularly preferably 2-5.

That is, a preferable synthesis method of the zirconium phosphate represented by the formula (2) is a wet method or hydrothermal method with ammonia or a salt thereof.

Upon synthesis of the zirconium phosphate represented by the formula (2), a molar ratio of phosphoric acid or salt thereof to oxalic acid or salt thereof (assuming that oxalic acid or salt thereof is 1) is preferably 1-6, more preferably 1.5-5, further more preferably 1.51-4 and particularly preferably 1.52-3.5. When it is synthesized by a hydrothermal method, oxalic acid or a salt thereof is not an essential component, and the amount to be used thereof can be appropriately adjusted.

That is, a preferable synthesis method of the zirconium phosphate represented by the formula (2) is a wet method or hydrothermal method with oxalic acid or a salt thereof.

The solid content in a reaction slurry for synthesis of the zirconium phosphate represented by the formula (2) is preferably 3 wt % or more, and in consideration of efficiency such as economy, more preferably 7-15%.

The pH upon synthesis of the zirconium phosphate represented by the formula (2) is preferably not less than 1 and not more than 4, more preferably 1.5-3.5, further more preferably 2-3 and particularly preferably 2.2-3. When the pH exceeds 4, the zirconium phosphate represented by the formula (2) may not be synthesized. When the pH is less than 1, the zirconium phosphate represented by the formula (2) may not be synthesized. For the adjustment of the pH, sodium hydroxide, potassium hydroxide or aqueous ammonia is preferably used, and more preferably sodium hydroxide is used.

The temperature upon synthesis of the zirconium phosphate represented by the formula (2) is preferably not less than 70° C., more preferably not less than 80° C., further more preferably not less than 90° C. and particularly preferably not less than 95° C. Also, as the synthesis temperature, a temperature of not more than 170° C. is preferable and not more than 150° C. is more preferable. When the temperature is less than 70° C., the zirconium phosphate of the present invention may not be synthesized. When the temperature exceeds 170° C., the synthesis is energetically disadvantageous.

When the zirconium phosphate represented by the formula (2) is synthesized, it is desirable that the raw materials are homogeneously mixed and stirred so as to effect the reaction to uniformly proceed.

The time for synthesizing the zirconium phosphate represented by the formula (2) differs depending upon the synthesis temperature. For example, the time for synthesizing the zirconium phosphate of the present invention is preferably not less than 2 hours, more preferably 3-72 hours and further more preferably 4-48 hours.

The zirconium phosphate represented by the formula (2) can be synthesized as a compound with a median diameter of 0.1-5 μm. The median diameter of the zirconium phosphate represented by the formula (2) is preferably 0.1-5 μm, more preferably 0.2-3 μm and further more preferably 0.3-2 μm. Meanwhile, in consideration of processability into various products, in addition to the median diameter, the maximum particle diameter is also important. Therefore, the maximum particle diameter of the zirconium phosphate represented by the formula (2) is preferably not more than 10 μm, further preferably not more than 8 μm and particularly preferably not more than 6 μm from the viewpoint of the effect.

As the zirconium phosphate represented by the formula (2) which can be used as a raw material of the silver based inorganic antibacterial agent of the present invention, the followings can be exemplified. However, those with ammonium ion are low in ion exchange property, and thus if a high conversion to silver ion is desired, there may be a case where ammonium ion should be allowed to leave to obtain an H type which is high in ion exchange property by conducting calcination or the like as required.

$(NH_4)_{1.4}Zr_{1.88}Hf_{0.02}(PO_4)_3 \cdot 0.05H_2O$
$(NH_4)_{1.24}Zr_{1.92}Hf_{0.02}(PO_4)_3 \cdot 0.15H_2O$
$Na_{0.6}(NH_4)_{0.84}Zr_{1.87}Hf_{0.02}(PO_4)_3 \cdot 0.3H_2O$
$Na_1(NH_4)_{0.44}Zr_{1.87}Hf_{0.02}(PO_4)_3 \cdot 0.2H_2O$
$Na_{0.6}H_{0.3}(NH_4)_{0.42}Zr_{1.90}Hf_{0.02}(PO_4)_3 \cdot 0.2H_2O$
$K_{0.92}(NH_4)_{0.44}Zr_{1.89}Hf_{0.02}(PO_4)_3 \cdot 0.1H_2O$
$Na_{0.72}(NH_4)Zr_{1.80}Hf_{0.02}(PO_4)_3 \cdot 0.2H_2O$
$Na_{0.3}H_{0.34}(NH_4)Zr_{1.82}Hf_{0.02}(PO_4)_3 \cdot 0.1H_2O$
$Na(NH_4)_{0.76}Zr_{1.79}Hf_{0.02}(PO_4)_3 \cdot 0.1H_2O$
$Na_{0.6}H_{0.4}(NH_4)_{0.6}Zr_{1.83}Hf_{0.02}(PO_4)_3 \cdot 0.3H_2O$
$Na_{1.2}Zr_{1.93}Hf_{0.02}(PO_4)_3 \cdot 0.1H_2O$
$Na_{0.24}H_{1.36}Zr_{1.83}Hf_{0.02}(PO_4)_3 \cdot 0.11H_2O$
$H_{1.4}Zr_{1.88}Hf_{0.02}(PO_4)_3 \cdot 0.15H_2O$
$K_{0.6}H_{0.6}Zr_{1.93}Hf_{0.02}(PO_4)_3 \cdot 0.1H_2O$
$Na_{1.12}Zr_{1.95}Hf_{0.02}(PO_4)_3$
$NaH_{0.12}Zr_{1.95}Hf_{0.02}(PO_4)_3$
$Na_{1.48}Zr_{1.86}Hf_{0.02}(PO_4)_3$
$Na_{0.48}HZr_{1.86}Hf_{0.02}(PO_4)_3$
$Na_{0.72}HZr_{1.80}Hf_{0.02}(PO_4)_3$
$Na_{0.6}H_{1.12}Zr_{1.80}Hf_{0.02}(PO_4)_3$
$Na_{0.6}(NH_4)_{0.4}Zr_{1.98}Hf_{0.02}(PO_4)_3 \cdot 0.09H_2O$
$Na_{1.0}(NH_4)_{0.6}Zr_{1.83}Hf_{0.02}(PO_4)_3 \cdot 0.09H_2O$
$Na_{0.8}(NH_4)_{0.4}Zr_{1.93}Hf_{0.02}(PO_4)_3 \cdot 0.09H_2O$
$Na_{0.5}(NH_4)_{0.7}Zr_{1.93}Hf_{0.02}(PO_4)_3 \cdot 0.1H_2O$
$Na_{0.24}(NH_4)_{1.36}Zr_{1.83}Hf_{0.02}(PO_4)_3 \cdot 0.11H_2O$
$(NH_4)_{1.4}Zr_{1.88}Hf_{0.02}(PO_4)_3 \cdot 0.15H_2O$
$Na_{0.8}(NH_4)_{0.4}Zr_{1.93}Hf_{0.02}(PO_4)_3 \cdot 0.09H_2O$ In order to obtain the silver based inorganic antibacterial agent of the present invention, a silver ion must be added to the zirconium phosphate represented by the formula (2). The addition of the silver ion can be performed by ion exchange, and this method can be performed by immersing the zirconium phosphate represented by the formula (2) in an aqueous solution containing a silver ion at an appropriate concentration. Also, when the immersion is conducted, it is preferable to provide a condition under which they are uniformly mixed by stirring or the like. The amount to be immersed only has to meet a concentration at which uniform mixing with the aqueous solution can be conducted. For this purpose, the concentration of the zirconium phosphate represented by the formula (2) is preferably not more than 30 weight %. As the aqueous solution containing a silver ion, preferably used is an aqueous solution which is made by dissolving silver nitrate in ion exchanged water. The temperature of the aqueous solution during ion exchange is usually 0-100° C. and preferably 20-80° C. Since the ion exchange proceeds immediately, the time for immersion may be not more than 5 minutes, but is preferably from 30 minutes to 5 hours in order to attain a high silver ion conversion uniformly. The silver ion exchange will not proceed further if the time for immersion is extended to 5 hours or more.

After the completion of the silver ion exchange, the reaction product is well washed with ion exchange water and the like, and then dried to obtain a silver based inorganic antibacterial agent of the present invention in which a silver ion is retained by the zirconium phosphate represented by the formula (2).

In order to improve colorlessness of the silver based inorganic antibacterial agent of the present invention, it is preferable to calcine the above obtained silver based inorganic antibacterial agent. For improving colorlessness, calcining can be performed for one which has not been subjected to silver ion exchange (that is, the zirconium phosphate represented by the formula (2)), but for obtaining sufficient colorlessness, calcining is preferably performed after silver ion exchange has been performed. The calcining temperature is preferably 550-1000° C., more preferably 600-900° C., and further more preferably 630-800° C. for improvement of colorlessness. Also, the time for calcining is preferably not less than 1 hour, more preferably not less than 2 hours, and further more preferably not less than 4 hours for improvement of colorlessness. The time for calcining is preferably not more than 48 hours and further preferably not more than 36 hours.

After the completion of calcining, the resultant may absorb moisture when it is left for long time, and thus it is preferably cooled within 24 hours and further preferably within 18 hours. Since the silver based inorganic antibacterial agent of the present invention may sometimes be aggregated after calcined, aggregated one may be pulverized using a pulverizer. In this case, the time for pulverizing should be short considering moisture absorbability or the like.

The followings can be illustrated as the silver based inorganic antibacterial agents of the present invention.

$Ag_{0.2}H_{1.2}Zr_{1.88}Hf_{0.02}(PO_4)_3 \cdot 0.05H_2O$
$Ag_{0.1}H_{1.14}Zr_{1.92}Hf_{0.02}(PO_4)_3 \cdot 0.15H_2O$
$Ag_{0.2}Na_{0.4}(NH_4)_{0.84}Zr_{1.87}Hf_{0.02}(PO_4)_3 \cdot 0.3H_2O$
$Ag_{0.3}Na_{0.1}H_{1.04}Zr_{1.87}Hf_{0.02}(PO_4)_3 \cdot 0.2H_2O$
$Ag_{0.5}Na_{0.2}H_{0.3}(NH_4)_{0.32}Zr_{1.90}Hf_{0.02}(PO_4)_3 \cdot 0.2H_2O$
$Ag_{0.4}K_{0.6}H_{0.36}Zr_{1.89}Hf_{0.02}(PO_4)_3 \cdot 0.1H_2O$
$Ag_{0.07}Na_{0.38}H_{0.55}Zr_{1.98}Hf_{0.02}(PO_4)_3 \cdot 0.1H_2O$
$Ag_{0.17}Na_{0.07}H_{1.36}Zr_{1.83}Hf_{0.02}(PO_4)_3 \cdot 0.11H_2O$
$Ag_{0.46}Na_{0.4}H_{0.34}Zr_{1.93}Hf_{0.02}(PO_4)_3 \cdot 0.12H_2O$ The form of use of the silver based inorganic antibacterial agent of the present invention is not particularly limited, and it can be appropriately mixed with another component or can be combined with another material according to use. For example, it can be used in various forms including powder, powder-containing dispersion, powder-containing particle, powder-containing paint, powder-containing fiber, powder-containing paper, powder-containing plastic, powder-containing film and powder-containing aerosol. Further, it can be used in combination with various additive agents or materials such as deodorant, fire-extinguishing agent, anti-corrosive agent, fertilizer and building materials, as required.

The silver based inorganic antibacterial agent of the present invention can be mixed with various additives if required, in order to improve processability for kneading into the resin and other properties. Concrete examples thereof include pigments such as zinc oxide and titanium oxide, inorganic ion exchangers such as zirconium phosphate and zeolite, dyes, antioxidants, light stabilizers, flame retardants, antistatic agents, foaming agents, impact resistance reinforcements, glass fibers, lubricants such as metal soap, desiccants, expanders, coupling agents, nucleators, fluidity improvers, deodorants, wood powder, anti-fungal agents, antifouling agents, rust preventives, metal powder, ultraviolet absorbers, and ultraviolet screeners.

The antibacterial resin composition can easily be obtained by blending the silver based inorganic antibacterial agent of the present invention with a resin. A kind of resin which can be used is not particularly limited, and is any of natural resins, synthetic resins and semi-synthetic resins, and also any of thermoplastic resins and thermosetting resins. Concrete resins may be any of resins for molding, resins for fiber or rubbery resins, including, for example, resins for molding or fiber such as polyethylene, polypropylene, vinyl chloride, ABS resin, AS resin, MBS resin, nylon resin, polyester, polyvinylidene chloride, polystyrene, polyacetal, polycarbonate, PBT, acrylic resin, fluorocarbon polymer, polyurethane elastomer, polyester elastomer, melamine, urea resin, polytetrafluoroethylene resin, unsaturated polyester resin, rayon, acetate, acryl, polyvinyl alcohol, cupra, triacetate and vinylidene; and rubbery resins such as natural rubber, silicone rubber, styrene butadiene rubber, ethylene propylene rubber, fluoro rubber, nitrile rubber, chlorosulfonated polyethylene rubber, butadiene rubber, synthetic natural rubber, butyl rubber, urethane rubber and acrylic rubber. In addition, antibacterial fiber can be produced by combining the silver based inorganic antibacterial agent of the present invention with a fiber of natural fibers.

The blending proportion of the silver based inorganic antibacterial agent of the present invention in the above antibacterial resin composition is preferably 0.03-10 parts by weight and more preferably 0.1-5 parts by weight based on 100 parts by weight of the antibacterial resin composition. When the proportion is less than 0.03 part by weight, antibacterial property of the antibacterial resin composition may be insufficient. On the other hand, when the proportion is more than 10 parts by weight, further improvement of antibacterial effect is hardly expected, and thus it is uneconomical and may considerably lower the properties of resin.

As a method of blending the silver based inorganic antibacterial agent of the present invention with a resin to make a resin molded article, the conventional methods can be adopted. Examples thereof are (1) a method in which a pellet resin or powder resin is directly mixed in a mixer using an impregnation agent for facilitating attachment of the silver based inorganic antibacterial agent powder to a resin or dispersing agent for improving dispersibility of the antibacterial agent powder, (2) a method in which mixing is conducted as described in the above method, followed by molding the mixture into a pellet form in an extrusion-molding machine, and then the molded product is blended with a pellet resin, (3) a method in which the silver based inorganic antibacterial agent is molded into a highly concentrated pellet form using a wax, and then the pelletized molded product is blended with a pellet resin, and (4) a method in which a paste like composition is prepared by dispersing and mixing the silver based inorganic antibacterial agent in a highly viscous liquid such as a polyol, and then the paste is blended with a pellet resin.

For molding the above antibacterial resin composition, conventional processing techniques and machines can be used according to characteristics of various resins. That is, it can be molded easily by means of mixing, mingling or kneading at an appropriate temperature or pressure, for example, under heating and pressurizing or depressurizing. Their specific operations only have to follow the ordinary methods, so as to mold and process into various forms such as lump form, sponge form, film form, sheet form, thread form, pipe form or combination of these.

The form of use of the silver based inorganic antibacterial agent of the present invention is not particularly limited, and is not limited to blending with a resin molded product or polymer compound. It can be properly mixed with other components or combined with other materials in accordance with uses that require antifungal, anti-algae and antibacterial properties. For example, it can be used in various forms such as powder form, powder dispersion form, granular form, aerosol form, or liquid form.

Uses

The silver based inorganic antibacterial agent of the present invention can be used in various fields which require antifungal, anti-algae and antibacterial properties, that is, electrical products, kitchen products, fiber products, house or building material products, toiletry products, paper products, toys, leather products, stationery and other products.

Further, concrete applications are exemplified by electrical products such as dishwashers, dishdryers, refrigerators, washing machines, pots, televisions, personal computers, radio cassette recorders, cameras, video cameras, water purifiers, rice cookers, vegetable cutters, registers, bedding dryers, fax machines, ventilating fans, and air conditioners; and kitchen products such as dishes, cutting boards, cutters, trays, chopsticks, teapots, thermos bottles, knives, grips of ladles, spatulas, lunch boxes, rice scoops, bowls, strainer baskets, triangle corners, scourer cases, rubbish baskets and strainer bags.

Examples of fiber products are shower curtains, bedding cottons, air conditioner filters, panty hoses, socks, small damp towels, bed sheets, bedding covers, pillow, gloves, aprons, curtains, nappies, bandages, masks and sport wear; and examples of house or building material products are decorative boards, wall paper, floor boards, films for window, handles, lags, mats, artificial marbles, handrails, joints, tiles and waxes. Examples of toiletry products are toilet seats, bathtubs, tiles, bedpans, dirt cases, toilet brushes, bath covers, pumice, soap cases, bath chairs, cloth basket, showers and washstands; examples of paper products are wrapping paper, drug packing paper, medicine chests, sketchbooks, medical records, notebooks and origamis; and examples of toys are doll, stuffed toys, paper clays, blocks and puzzles.

Further, examples of leather products are shoes, bags, belts, watch bands, interior equipment, chairs, gloves and straps; and examples of stationery are ballpoint pens, mechanical pens, pencils, erasers, crayons, paper, diaries, flexible disks, rulers, post-it and staplers.

Examples of other products are insoles, cosmetic containers, scourers, powder puffs, hearing aids, musical instruments, cigarette filters, adhesive paper sheets for cleaning, strap grips, sponges, kitchen towels, cards, microphones, barbar tools, vender machines, shavers, telephones, thermometers, stethoscopes, slippers, clothes cases, teeth brushes, sand for sandpits, food wrapping films, antibacterial sprays and paints.

EXAMPLE

Hereinafter, the present invention will be described in detail by way of working examples. However, the present invention is not limited to these.

The median diameter was measured by using a laser diffraction particle analyzer on volume basis.

The amounts of zirconium, hafnium, phosphorus, sodium, potassium and silver were calculated by dissolving a sample using a strong acid, and then measuring the resulting liquid by an ICP emission spectrometer. The amount of ammonia was calculated by dissolving a sample using a strong acid, and then measuring the resulting liquid by indophenol method.

Synthesis Example 1

0.1 mol of oxalic acid dihydrate, 0.2 mol of zirconium oxychloride octahydrate containing 0.18% hafnium and 0.1 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.7, and then stirred at 98° C. for 14 hours. Then, the resulting precipitates were washed well, and dried at 120° C. to synthesize a zirconium phosphate compound.

As a result of measurement of the composition and the like of the zirconium phosphate, the compositional formula was found as follows:

$$Na_{0.6}(NH_4)_{0.4}Zr_{1.98}Hf_{0.02}(PO_4)_3 \cdot 0.09H_2O,$$

and the median diameter was 0.65 μm.

Synthesis Example 2

0.1 mol of oxalic acid dihydrate, 0.19 mol of zirconium oxychloride octahydrate containing 0.18% hafnium and 0.13 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.7, and then stirred at 98° C. for 14 hours. Then, the resulting precipitates were washed well, and dried at 120° C. to synthesize a zirconium phosphate compound.

As a result of measurement of the composition and the like of the zirconium phosphate, the composition formula was found as follows:

$$Na_{1.0}(NH_4)_{0.6}Zr_{1.83}Hf_{0.02}(PO_4)_3 \cdot 0.09H_2O,$$

and the median diameter was 0.68 μm.

Synthesis Example 3

0.195 mol of zirconium oxychloride octahydrate containing 0.18% hafnium and 0.1 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.7, and then stirred at 140° C. under saturated vapor pressure for 4 hours. Then, the resulting precipitates were washed well, and dried at 120° C. to synthesize a zirconium phosphate compound.

As a result of measurement of the composition and the like of the zirconium phosphate, the composition formula was found as follows:

$$Na_{0.8}(NH_4)_{0.4}Zr_{1.93}Hf_{0.02}(PO_4)_3 \cdot 0.09H_2O,$$

and the median diameter was 0.55 μm.

Synthesis Example 4

0.1 mol of oxalic acid dihydrate, 0.195 mol of zirconium oxychloride octahydrate containing 0.18% hafnium and 0.11 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.9, and then stirred at 98° C. for 14 hours. Then, the resulting precipitates were washed well, and dried at 120° C. to synthesize a zirconium phosphate.

As a result of measurement of the composition and the like of the zirconium phosphate, the composition formula was found as follows:

$$Na_{0.5}(NH_4)_{0.7}Zr_{1.93}Hf_{0.02}(PO_4)_3 \cdot 0.1H_2O,$$

and the median diameter was 0.55 μm.

Synthesis Example 5

0.1 mol of oxalic acid dihydrate, 0.185 mol of zirconium oxychloride octahydrate containing 0.18% hafnium and 0.14 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.9, and then stirred at 98° C. for 14 hours. Then, the resulting precipitates were washed well, and dried at 120° C. to synthesize a zirconium phosphate.

As a result of measurement of the composition and the like of the zirconium phosphate, the composition formula was found as follows:

$$Na_{0.24}(NH_4)_{1.36}Zr_{1.83}Hf_{0.02}(PO_4)_3 \cdot 0.11H_2O,$$

and the median diameter was 0.44 μm.

Synthesis Example 6

0.1 mol of oxalic acid dihydrate and 0.19 mol of zirconium oxychloride octahydrate containing 0.18% hafnium were dissolved in 300 ml of deionized water, and then 0.3 mol of phosphoric acid was added thereto under stirring. A 28% aqueous ammonia solution was added to the solution to adjust the pH to 2.9, and then stirred at 98° C. for 14 hours. Then, the resulting precipitates were washed well, and dried at 120° C. to synthesize a zirconium phosphate.

As a result of measurement of the composition and the like of the zirconium phosphate, the composition formula was found as follows:

$(NH_4)_{1.4}Zr_{1.88}Hf_{0.02}(PO_4)_3 \cdot 0.15H_2O$, and the median diameter was 0.42 μm.

Synthesis Example 7

0.1 mol of oxalic acid dihydrate, 0.195 mol of zirconium oxychloride octahydrate containing 0.18% hafnium and 0.07 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.7, and then stirred at 98° C. for 14 hours. Then, the resulting precipitates were washed well, and dried at 120° C. to synthesize a zirconium phosphate.

As a result of measurement of the composition and the like of the zirconium phosphate, the composition formula was found as follows:

$Na_{0.8}(NH_4)_{0.4}Zr_{1.93}Hf_{0.02}(PO_4)_3 \cdot 0.09H_2O$, and the median diameter was 0.60 μm.

Synthesis Example 8

0.1 mol of oxalic acid dihydrate and 0.195 mol of zirconium oxychloride octahydrate containing 0.18% hafnium were dissolved in 300 ml of deionized water, and then 0.3 mol of phosphoric acid was added thereto under stirring. A 20% aqueous sodium hydroxide solution was added to the solution to adjust the pH to 2.7, and then stirred at 98° C. for 14 hours. Then, the resulting precipitates were washed well, and dried at 120° C. to synthesize a zirconium phosphate.

As a result of measurement of the composition and the like of the zirconium phosphate, the composition formula was found as follows:

$Na_{1.2}Zr_{1.93}Hf_{0.02}(PO_4)_3 \cdot 0.1H_2O$, and the median diameter was 0.64 μm.

Synthesis Example 9

0.1 mol of oxalic acid dihydrate, 0.185 mol of zirconium oxychloride octahydrate containing 0.18% hafnium and 0.14 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.9, and then stirred at 98° C. for 14 hours. Then, the resulting precipitates were washed well, dried at 120° C., and further calcined at 700° C. for 4 hours to synthesize a zirconium phosphate.

As a result of measurement of the composition and the like of the zirconium phosphate, the composition formula was found as follows:

$Na_{0.24}H_{1.36}Zr_{1.83}Hf_{0.02}(PO_4)_3 \cdot 0.11H_2O$, and the median diameter was 0.43 μm.

Synthesis Example 10

0.1 mol of oxalic acid dihydrate and 0.19 mol of zirconium oxychloride octahydrate containing 0.18% hafnium were dissolved in 300 ml of deionized water, and then 0.3 mol of phosphoric acid was added thereto under stirring. A 28% aqueous ammonia solution was added to the solution to adjust the pH to 2.9, and then stirred at 98° C. for 14 hours. Then, the resulting precipitates were washed well, dried at 120° C., and further calcined at 700° C. for 4 hours to synthesize a zirconium phosphate.

As a result of measurement of the composition and the like of the zirconium phosphate, the composition formula was found as follows:

$H_{1.4}Zr_{1.88}Hf_{0.02}(PO_4)_3 \cdot 0.15H_2O$, and the median diameter was 0.34 μm.

Example 1

To 0.004 mol of silver nitrate in 450 ml of a 1N aqueous nitric acid solution, 0.09 mol of the zirconium phosphate synthesized in Synthesis Example 1 was added, and stirred at 60° C. for 2 hours to retain a silver ion. Then, it was washed well, dried at 120° C. and then calcined at 720° C. for 4 hours. The calcined powder was lightly pulverized to obtain a silver based inorganic antibacterial agent of the present invention.

As a result of measurement of the composition of the silver based inorganic antibacterial agent, the composition formula was found as follows:

$Ag_{0.07}Na_{0.38}H_{0.55}Zr_{1.98}Hf_{0.02}(PO_4)_3 \cdot 0.1H_2O$.

Median diameter (μm), maximum particle diameter (μm) and minimum inhibitory concentration (MIC, μg/ml) against *Escherichia coli* of the silver based inorganic antibacterial agent were measured, and these results are shown in Table 1.

Example 2

To 0.015 mol of silver nitrate in 450 ml of a 1N aqueous nitric acid solution, 0.09 mol of the zirconium phosphate synthesized in Synthesis Example 2 was added, and stirred at 60° C. for 2 hours to retain a silver ion. Then, it was washed well, dried at 120° C. and then calcined at 720° C. for 4 hours. The calcined powder was lightly pulverized to obtain a silver based inorganic antibacterial agent of the present invention.

As a result of measurement of the composition of the silver based inorganic antibacterial agent, the composition formula was found as follows:

$Ag_{0.17}Na_{0.07}H_{1.36}Zr_{1.83}Hf_{0.02}(PO_4)_3 \cdot 0.11H_2O$.

Median diameter (μm), maximum particle diameter (μm) and minimum inhibitory concentration (MIC, μg/ml) against *Escherichia coli* of the silver based inorganic antibacterial agent were measured, and these results are shown in Table 1.

Example 3

To 0.045 mol of silver nitrate in 450 ml of a 1N aqueous nitric acid solution, 0.09 mol of the zirconium phosphate synthesized in Synthesis Example 3 was added, and stirred at 60° C. for 2 hours to retain a silver ion. Then, it was washed well, dried at 120° C. and then calcined at 700° C. for 4 hours. The calcined powder was lightly pulverized to obtain a silver based inorganic antibacterial agent of the present invention.

As a result of measurement of the composition of the silver based inorganic antibacterial agent, the composition formula was found as follows:

$Ag_{0.46}Na_{0.4}H_{0.34}Zr_{1.93}Hf_{0.02}(PO_4)_3 \cdot 0.12H_2O$.

Median diameter (μm), maximum particle diameter (μm) and minimum inhibitory concentration (MIC, μg/ml) against Escherichia coli of the silver based inorganic antibacterial agent were measured, and these results are shown in Table 1.

Examples 4-10

Silver based inorganic antibacterial agents were obtained by the same procedure as in Example 1 except that the zirconium phosphate synthesized in Synthesis Example 1 was changed to a product which was synthesized in Synthesis Example 4, 5, 6, 7, 8, 9 or 10. MICS of these against *Escherichia coli* were comparable to Example 1.

Comparative Example 1

0.1 mol of oxalic acid dihydrate, 0.2 mol of zirconium oxychloride octahydrate and 0.05 mol of ammonium chloride were dissolved in 300 ml of deionized water, and then 0.3 mol of phosphoric acid was added thereto under stirring. A 20% aqueous sodium hydroxide solution was added to the solution to adjust the pH to 2.5, and then stirred at 98° C. for 14 hours. Then, the resulting precipitates were washed well, and dried at 120° C. to synthesize a zirconium phosphate compound.

To 0.004 mol of silver nitrate in 450 ml of a 1N aqueous nitric acid solution, 0.09 mol of the zirconium phosphate synthesized above was added, and the mixture was stirred at 60° C. for 2 hours to allow the zirconium phosphate to retain a silver ion. Then, the resulting precipitates were washed well and dried at 120° C., and then the resulting powder was lightly pulverized to obtain a comparative silver based inorganic antibacterial agent. As a result of measurement of the composition of the comparative silver based inorganic antibacterial agent, the composition formula was found as follows:

$Ag_{0.07}Na_{0.45}(NH_4)_{0.48}Zr_2(PO_4)_3 \cdot 0.11H_2O$.

Median diameter (μm), maximum particle diameter (μm) and minimum inhibitory concentration (MIC, μg/ml) against *Escherichia coli* of the comparative silver based inorganic antibacterial agent were measured, and these results are shown in Table 1.

Comparative Example 2

0.1 mol of oxalic acid dihydrate and 0.2 mol of zirconium oxychloride octahydrate were dissolved in 300 ml of deionized water, and then 0.3 mol of phosphoric acid was added thereto under stirring. A 20% aqueous sodium hydroxide solution was added to the solution to adjust the pH to 3.6, and then stirred at 98° C. for 14 hours. Then, the resulting precipitates were washed well, and dried at 120° C. to synthesize a zirconium phosphate compound.

To 0.015 mol of silver nitrate in 450 ml of a 1N aqueous nitric acid solution, 0.09 mol of the zirconium phosphate synthesized above was added, and stirred at 60° C. for 2 hours to retain a silver ion. Then, the resulting precipitates were washed well and dried at 120° C., and then calcined at 770° C. for 4 hours. The calcined powder was lightly pulverized to obtain a comparative silver based inorganic antibacterial agent. As a result of measurement of the composition of the comparative silver based inorganic antibacterial agent, the composition formula was found as follows:

$Ag_{0.17}Na_{0.83}Zr_2(PO_4)_3 \cdot 0.12H_2O$.

Median diameter (μm), median diameter, maximum particle diameter (μm) and minimum inhibitory concentration (MIC, μg/ml) against *Escherichia coli* of the comparative silver based inorganic antibacterial agent were measured, and these results are shown in Table 1.

Comparative Example 3

0.2 mol of zirconium oxychloride octahydrate and 0.05 mol of ammonium chloride were dissolved in 300 ml of deionized water, and then 0.3 mol of phosphoric acid was added thereto under stirring. A 20% aqueous sodium hydroxide solution was added to the solution to adjust the pH to 3.6, and then the resulting precipitates were washed well, and calcined at 900° C. By pulverizing a bulky product obtained by the calcination, a zirconium phosphate compound was synthesized.

To 0.045 mol of silver nitrate in 450 ml of a 1N aqueous nitric acid solution, 0.09 mol of the zirconium phosphate synthesized above was added, and stirred at 60° C. for 2 hours to retain a silver ion. Then, the resulting precipitates were washed well and dried at 120° C., and then calcined at 770° C. for 4 hours. The calcined powder was lightly pulverized to obtain a silver based inorganic antibacterial agent. As a result of measurement of the composition of the comparative silver based inorganic antibacterial agent, the composition formula was found as follows:

$Ag_{0.44}Na_{0.22}H_{0.34}Zr_2(PO_4)_3 \cdot 0.11H_2O$.

Median diameter (μm), maximum particle diameter (μm) and minimum inhibitory concentration (MIC, μg/ml) against *Escherichia coli* of the comparative silver based inorganic antibacterial agent were measured, and these results are shown in Table 1.

Comparative Example 4

To 450 ml of a solution of 0.045 mol of silver nitrate, 0.09 mol of an A-type zeolite commercially available was added, and stirred at 60° C. for 2 hours to retain a silver ion. Then, the resulting precipitates were washed well, and dried at 120° C. The dried powder was lightly pulverized to obtain a comparative silver based inorganic antibacterial agent. Median diameter (μm), maximum particle diameter (μm) and minimum inhibitory concentration (MIC, μg/ml) against *Escherichia coli* of the comparative silver based inorganic antibacterial agent were measured, and these results are shown in Table 1.

TABLE 1

| | Median diameter | Maximum particle diameter | MIC |
|---|---|---|---|
| Example 1 | 0.67 | 1.3 | 62.5 |
| Example 2 | 0.69 | 1.4 | 62.5 |
| Example 3 | 0.55 | 1.1 | 31.25 |
| Comparative Example 1 | 0.46 | 1.3 | 125 |
| Comparative Example 2 | 0.51 | 1.7 | 125 |
| Comparative Example 3 | 2.2 | 23.9 | 250 |
| Comparative Example 4 | 2.6 | 8.9 | 62.5 |

Example 11

Evaluation on Molded Article

The silver based inorganic antibacterial agent obtained in Example 1 was blended at a concentration of 0.15% with a nylon 6 resin available from Ube Industries, Ltd., and injection-molded at 280° C. to obtain a molded product a which was a plate of 2 mm in thickness. The color difference ΔE between the molded product a and a plate free from the antibacterial agent was measured using a colorimeter. The results are shown in Table 2. Also, the injection-molded plate was used to conduct an antibacterial test in accordance with "JIS 22801 5.2: Test methods for plastic products and the like". The results of the obtained antibacterial activity are also shown in Table 2.

Similarly, molded products b-c and comparative molded products d-g were produced using the silver based inorganic antibacterial agents and the comparative silver based inorganic antibacterial agents produced in Examples 2-3 and Comparative Examples 1-4. The color difference and antibacterial activity of these molded products were also measured, and the results thereof are shown in Table 2.

TABLE 2

|  | Color difference ΔE | Antibacterial activity | |
|---|---|---|---|
|  |  | *Staphylococcus aureus* | *Escherichia coli* |
| Molded product a (Example 1) | 2.9 | more than 4.5 | more than 6.2 |
| Molded product b (Example 2) | 3.3 | more than 4.5 | more than 6.2 |
| Molded product c (Example 3) | 3.8 | more than 4.5 | more than 6.2 |
| Comparative molded product d (Comparative Example 1) | 4.2 | 4.4 | 6.1 |
| Comparative molded product e (Comparative Example 2) | 27 | 4.0 | more than 6.2 |
| Comparative molded product f (Comparative Example 3) | 6.6 | 4.1 | 5.8 |
| Comparative molded product g (Comparative Example 4) | 42.3 | 4.1 | more than 6.2 |

Example 12

Evaluation on Coating 0.2 part by weight of the silver based inorganic antibacterial agent obtained in Example 1 was added to 100 parts by weight of a water based UV paint (acrylic based), and well stirred and dispersed. About 5 grams of the resulting dispersion was put on a 20 cm×10 cm OHP film, and uniform coating was produced by using bar coater (#60). The coating was dried at 50° C. for 10 minutes, and irradiated with UV at 80 W and 10 m/min to cure, thereby obtaining a coating a. Similarly, coatings b-c and comparative coatings d-g were produced by using the silver based inorganic antibacterial agents and the comparative silver based inorganic antibacterial agents produced in Examples 2-3 and Comparative Examples 1-4. The color of these coatings was measured using a colorimeter, and the results of the color difference ΔE from the color of a coating free from the antibacterial agent were shown in Table 3. Also, using these coatings, an antibacterial test was conducted in accordance with "JIS Z2801 5.2: Test methods for plastic products and the like", and the resulting antibacterial activity is shown in Table 3.

TABLE 3

|  | Color difference ΔE | Antibacterial activity | |
|---|---|---|---|
|  |  | *Staphylococcus Aureus* | *Escherichia coli* |
| Coating a (Example 1) | 7.6 | More than 4.7 | More than 6.1 |
| Coating b (Example 2) | 8.2 | More than 4.7 | More than 6.1 |
| Coating c (Example 3) | 8.2 | More than 4.7 | More than 6.1 |
| Comparative coating d (Comparative Example 1) | 9.3 | 4.5 | 5.7 |
| Comparative coating e (Comparative Example 2) | 36 | More than 4.7 | More than 6.1 |
| Comparative coating f (Comparative Example 3) | 4.6 | 4.4 | 5.8 |
| Comparative coating g (Comparative Example 4) | 55 | 4.2 | 5.6 |

Example 13

Nylon Spinning Test

The silver based inorganic antibacterial agent produced in Example 1 was blended at a concentration of 10 wt % with a nylon resin to produce a master batch. The master batch was mixed with nylon resin pellets to prepare an antibacterial resin containing the silver based inorganic antibacterial agent at a concentration of 0.3 wt %. Then, the antibacterial resin was melt-spun at the spinning temperature of 285° C. using a multi-filament spinning machine to obtain a nylon fiber (fiber a) containing the antibacterial agent with 24 filaments. Similarly, fibers b-c and comparative fibers d, e and g were produced using the silver based inorganic antibacterial agents and the comparative silver based inorganic antibacterial agents produced in Examples 2-3 and Comparative Examples 1, 2 and 4. Meanwhile, when the comparative silver based inorganic antibacterial agent of Comparative Example 3 was used, fibers were difficult to obtain. The resulting nylon fiber containing the antibacterial agent was scoured and washed 10 times, and then antibacterial property was evaluated by a quantitative test in accordance with JIS L 1902$^{-1998}$ using *Staphylococcus aureus* and the results thereof were shown in Table 4.

TABLE 4

|  |  | Antibacterial activity | |
|---|---|---|---|
|  | Yarn breakage | After scouring | After washing |
| Fiber a (Example 1) | None | More than 5.1 | More than 5.1 |
| Fiber b (Example 2) | None | More than 5.1 | More than 5.1 |
| Fiber c (Example 3) | None | More than 5.1 | More than 5.1 |
| Comparative fiber d (Comparative Example 1) | None | More than 5.1 | 4.4 |

TABLE 4-continued

| | Yarn breakage | Antibacterial activity | |
| --- | --- | --- | --- |
| | | After scouring | After washing |
| Comparative fiber e (Comparative Example 2) | None | More than 5.1 | 4.9 |
| Comparative fiber g (Comparative Example 4) | Some | More than 5.1 | 1.3 |

From these results, it is clear that the silver based inorganic antibacterial agent of the present invention is excellent in processability such as spinnability and also excellent in colorlessness when blended in the plastic products. In addition, better durability of the antibacterial effect was observed in the silver based inorganic antibacterial agents of the present invention compared with the existing silver based inorganic antibacterial agents.

INDUSTRIAL APPLICATION

The novel silver based inorganic antibacterial agent of the present invention is excellent in processability by virtue of homogeneous and fine particles, and also excellent in colorlessness and antibacterial properties in plastic products. Therefore, it is an antibacterial agent having high applicability to fine fibers, paints and other applications in which processability is of importance.

The invention claimed is:

1. A silver based inorganic antibacterial agent comprising, as an effective ingredient, a compound represented by the following general formula (1):

$$Ag_aM_bZr_cHf_d(PO_4)_3 \cdot nH_2O \quad (1)$$

wherein, in the formula (1), M is at least one ion selected from alkali metal ion, hydrogen ion and ammonium ion, a, b, c and d are positive numbers which satisfy $a+b+4(c+d)=9$, c and d satisfy $1.75<(c+d)<2.25$, and n is 0 or a positive number of not more than 2.

2. The silver based inorganic antibacterial agent according to claim 1, comprising a silver ion which is retained by ion exchange on a zirconium phosphate represented by the following general formula (2):

$$M_{b1}Zr_cHf_d(PO_4)_3 \cdot nH_2O \quad (2)$$

wherein, in the formula (2), M is at least one ion selected from alkali metal ion, hydrogen ion and ammonium ion, b1, c and d are positive numbers which satisfy $b1+4(c+d)=9$, c and d satisfy $1.75<(c+d)<2.25$, and n is a positive number of not more than 2.

3. The silver based inorganic antibacterial agent according to claim 2, wherein the zirconium phosphate represented by the general formula (2) is produced by a wet synthesis method or hydrothermal method.

4. An antibacterial product containing the silver based inorganic antibacterial agent according to claim 1.

* * * * *